United States Patent [19]

Steel et al.

[11] Patent Number: 5,858,648
[45] Date of Patent: Jan. 12, 1999

[54] ASSAYS USING REFERENCE MICROPARTICLES

[75] Inventors: James S. Steel, Rockville; Anne J. Bodner, Bethesda; Manish S. Kochar, Columbia; Glen M. Ford, Gaithersburg; John P. Huff, Finksburg, all of Md.

[73] Assignee: Sienna Biotech, Inc., Columbia, Md.

[21] Appl. No.: 743,164

[22] Filed: Nov. 4, 1996

[51] Int. Cl.[6] .......................... C12Q 1/70; G01N 33/554; G01N 33/546; G01N 33/545
[52] U.S. Cl. .......................... 435/5; 435/7.32; 435/7.36; 436/523; 436/529; 436/531; 436/533; 436/534; 436/805; 436/806
[58] Field of Search .................................... 436/523, 533, 436/529, 534, 531, 805, 806; 435/5, 7.32, 7.36

[56] References Cited

U.S. PATENT DOCUMENTS

| | | |
|---|---|---|
| 4,064,080 | 12/1977 | Daniel . |
| 4,072,576 | 2/1978 | Arwin et al. . |
| 4,174,952 | 11/1979 | Cannell et al. . |
| 4,181,636 | 1/1980 | Fischer . |
| 4,184,849 | 1/1980 | Cambiaso et al. . |
| 4,191,739 | 3/1980 | Uzgiris et al. . |
| 4,210,723 | 7/1980 | Dorman et al. . |
| 4,279,617 | 7/1981 | Masson et al. . |
| 4,305,925 | 12/1981 | Kapmeyer et al. . |
| 4,446,239 | 5/1984 | Tsuji et al. . |
| 4,521,521 | 6/1985 | Abbott et al. . |
| 4,851,329 | 7/1989 | Cohen et al. . |
| 5,284,748 | 2/1994 | Mroczkowski et al. . |
| 5,286,452 | 2/1994 | Hansen . |
| 5,369,037 | 11/1994 | Hansen . |
| 5,567,627 | 10/1996 | Lehnen . |
| 5,589,401 | 12/1996 | Hansen et al. . |

FOREIGN PATENT DOCUMENTS

WO/15193  7/1994  WIPO .

OTHER PUBLICATIONS

Masson, et al., Meth. Enzymol. 74:106–141 (1981).
Newman, et al., Ann. Clin. Biochem. 29:22–42 (1992).
Limet, et al., J. Immunol. Meth. 28:25–32 (1979).

*Primary Examiner*—David Saunders
*Assistant Examiner*—Patrick J. Nolan
*Attorney, Agent, or Firm*—Lerner, David, Littenberg, Krumholz & Mentlik

[57] ABSTRACT

Disclosed is an assay for determining the presence of at least one analyte in a sample, which involves the steps of: (a) mixing the sample and predetermined amounts of first test microparticles having disposed thereon a binding molecule which binds a first analyte, and inert reference microparticles to form a reaction mixture, and to allow for the first binding molecule to bind the first analyte; b) counting the numbers of the non-reacted first test microparticles and the reference microparticles; and (c) comparing the number of non-reacted first test microparticles to the reference microparticles to thereby establish a first test value so that the presence of the first analyte in the sample may be determined. In a preferred embodiment, the first test value is compared to a control value for a non-reactive sample, and a change value is calculated therefrom. The presence of additional analytes may be determined by adding second test microparticles having disposed thereon a second binding molecule which binds a second analyte, wherein the second test microparticles are resolvable against the first test microparticles and the reference microparticles in the given counting method, and comparing the number of non-reacted second test microparticles to the reference microparticles to establish a second test value. Also disclosed are compositions and kits containing the microparticles.

37 Claims, 1 Drawing Sheet

ASSAYS USING REFERENCE MICROPARTICLES

FIELD OF THE INVENTION

The present invention relates to the field of diagnostics, and more particularly to the use of assays to detect the presence of an analyte of interest in a given fluid.

BACKGROUND OF THE INVENTION

The agglutination reaction has long been used in qualitative and quantitative assays for a wide variety of bacteria, cell-surface antigens, serum proteins and other analytes of clinical interest. Agglutination usually results from the reaction between antibodies and antigens of interest to produce aggregates which can be detected and/or measured in various ways. In a typical agglutination assay format, particles such as polystyrene microparticles (commonly known as "latex") are coated with a material which binds an antigen of interest, and the coated particles are mixed with a sample, such as blood or other bodily fluid. Depending upon the particular antigen, the interaction may cause the particles to agglutinate with one another, or it may retard agglutination. In either case, the number of agglutinated particles present after the particles are reacted with the bodily fluid will indicate the amount of the antigen present. The same types of reaction have been utilized for the detection of specific antibodies by the agglutination reaction caused by the addition of the corresponding antigen which binds the antibody.

A number of particle-based immunoassays have been developed to exploit the specificity of antigen-antibody reactions, while avoiding the problems associated with conventional diagnostic methodology such as radiochemical labeling. For example, turbidimetric and nephelometric methods monitor light scattered from many particles in bulk solution. The former technique measures light transmission through a suspension of particle aggregates, whereas the latter technique directly measures scattered light in specific directions. These methods offer the advantage of not requiring a separation step; however, they have proven satisfactory only for the analysis of single analytes in a sample.

Several agglutination assays have been developed using optical flow particle analyzers that sense aggregate formation or the degree of non-agglutination, by the measurement of forward scattered light using particles having different sizes. The presence and/or amount of an analyte in a sample has been determined by measuring the extent of agglutination or the number of non-reacted or non-agglutinated particles. The agglutination assay disclosed in U.S. Pat. No. 4,279,617, to Masson et al., involves the steps of mixing a liquid sample with a first particulate reagent which binds the antigen or antibody of interest to form a complex, and then adding to the mixture a second, different particulate reagent which binds to the complex to form an agglutinate, but which does not bind with the free first particulate reagent. The presence or the amount of the antigen or antibody is determined by assaying the non-agglutinated first or second particulate reagent. Thus, to conduct a qualitative assay, the '617 patent teaches that it is merely necessary to count the number of first reagent particles remaining free in the reaction mixture, and then compare the result with the number of such particles added in the first step. In a later published article in Meth. Enzymol. 74:106–141 (1981), Masson et al. coined the acronym PACIA (particle counting immunoassay) to describe agglutination assays that involve counting the number of free or non-reacted particles as an indication of the presence of an analyte in a sample. Masson discloses the use of an AutoCounter to measure forward light scatter from only non-agglutinated particles within a certain size range, to the exclusion of all other particles. The PACIA method, however, has limited use, particularly due to inaccuracies caused by non-specific aggregation reactions and rheumatoid factor interference. See, Newman, et al., Ann. Clin. Biochem. 29:22–42 (1992), and Limet, et al., J. Immunol. Meth. 28:25–32 (1979).

U.S. Pat. No. 4,184,849 to Cambiaso et al. also teaches the use of optical counting system such as an AutoCounter in an agglutination assay, wherein the presence of antibodies or antigens in a liquid is detected by mixing the sample with two different particulate reagents which mutually agglutinate, but which agglutination is inhibited by the particular antibody or antigen being assayed. The amount of antigen or antibody present in the sample may be measured by determining the extent of agglutination or non-agglutination, the latter by simply counting the non-agglutinated particles or by using an identifying label.

U.S. Pat. No. 4,191,739 to Uzgiris, et al., is directed to an agglutination assay wherein the presence of a protein in a sample is determined by detecting multiplets of particles having a size formed by aggregation of only those particles having a first predetermined size with particles having a second predetermined size, using resistive pulse analysis. The method purports to enhance the accuracy of the assay by accounting for the initial distribution of non-specifically formed multiplets.

U.S. Pat. No. 4,851,329 to Cohen, et al., is directed to an agglutination assay wherein the cluster size distribution of the agglutinated particles is determined by optical pulse particle size analysis. A standard quantitative relationship may be established by measuring the ratio of a number of particle dimers to the number of particle monomers, or any other measure of cluster size distribution, in a given serial dilution of known concentration of analyte.

These assay methods are limited to single analyte analysis. Accordingly, there remains a need for an agglutination assay for the simultaneous measurement of a plurality of analytes in a given sample, and which also offers greater precision by reducing the effect of dilution errors, instrumentation flaws, and the like, on the assay results.

SUMMARY OF THE INVENTION

One aspect of the present invention is directed to an assay for determining the presence of an analyte in a sample, which involves the following steps:

(a) mixing the sample and predetermined amounts or ratios of test microparticles having disposed thereon a binding molecule which binds the analyte, and reference microparticles non-reactable with the analyte and the binding molecule, to form a liquid reaction mixture and to allow for the binding molecule to bind the analyte;

(b) counting the numbers of the reference microparticles and non-reacted test microparticles; and (c) comparing the number of non-reacted test microparticles to the reference microparticles - to thereby establish a test value so that the presence of the analyte in the sample can be determined.

Preferably, the assay method also includes the further step (d) of comparing the test value to a control value for a non-reactive sample which does not contain the analyte, in which case the presence of the analyte in the sample is then determined by calculating a change value from the test value and the control value. In a more preferred embodiment, the test value is the ratio of the number of non-reacted test microparticles to the number of reference microparticles found in step (c) after the reaction. The control value found in step (d) is the ratio of the number of non-reacted test microparticles to the number of reference microparticles obtained using the same procedures with the non-reactive sample. Thus, the control value may be referred to as the "control ratio", and the test value may be referred to as the "test ratio". The change value may be calculated by obtaining the difference between the control ratio and the test ratio, and dividing that difference by the control ratio. The result may be expressed as a percentage. In a more preferred embodiment, the change value is calculated by dividing the control ratio by the test ratio, and this result may also be expressed as a percentage.

Methods in accordance with this aspect of the present invention provide significant advantages. Because the test and control values represent loss of non-agglutinated particles, rather than formation of particular agglutinates in a particular size range, inaccuracies caused by formation of larger or smaller agglutinates are substantially eliminated. In addition, because the test value and control value are computed as a relationship between the number of non-agglutinated test microparticles and the number of inert reference particles, such as the test ratio and control ratio discussed above, errors due to inaccuracies in dilution of the reaction mixture and inaccuracies in particle counting are also substantially eliminated. The method further provides increased resolution of each type of test particle, thus allowing for multiple simultaneous tests. It also reduces inaccuracies inherent in counting large aggregates of particles.

The reference microparticles further enhance the accuracy and precision of the assays of the present invention because they serve as an overall on-board diagnostic for both the instrumentation and the assay method per se. The quality of the response generated by the reference microparticles, such as histogram width or rate of microparticles detected, may be indicative of a systemic disturbance involving fluid (e.g., clogging), electrical or optical features of the system. Aggregation of reference microparticles, e.g., dimerization, trimerization, etc., above a predetermined arbitrary value may be indicative of nonspecific binding of the test microparticles. The reference microparticles further enhance dilution accuracy as a function of the rate at which they are counted. They can identify or otherwise account for phenomena such as system drift.

Another aspect of the present invention is directed to an assay for determining the presence of at least two analytes in a sample, which involves the following steps:

(a) mixing the sample and predetermined amounts or ratios of first test microparticles having disposed thereon a first binding molecule which binds a first analyte, second test microparticles having disposed thereon a second binding molecule which binds a second analyte, and reference microparticles non-reactable with the first and second analytes and the first and second binding molecules, to form a reaction mixture and allow for the first binding molecule to bind the first analyte, and the second binding molecule to bind the second analyte;

(b) counting the numbers of the non-reacted first test microparticles, the non-reacted second test microparticles and the reference microparticles; and (c) comparing the number of non-reacted first test microparticles to the reference microparticles to thereby establish a first test value, and comparing the number of non-reacted second test microparticles to the reference microparticles to thereby establish a second test value, so that the presence of the first and second analytes in the sample may be determined.

This aspect of the present invention preferably includes the further step (d) of comparing the first test value to a first control value for a non-reactive sample (which does not contain the first analyte) to determine the presence of the first analyte, and comparing said second test value to a second control value for a non-reactive sample (which does not contain the second analyte), to determine the presence of the second analyte. The assay will accommodate simultaneous multiple analyte analysis of a single sample, as well as providing the advantages discussed above. Additional test microparticles are used if more than two analytes are to be measured.

Yet another aspect of the present invention is directed to a kit for use in an assay for determining the presence of an analyte in a sample. The kit contains the following elements:

(a) test microparticles having disposed thereon a binding molecule which binds the analyte; and (b) reference microparticles non-reactable with the analyte, the test microparticles and the binding molecule;

wherein the test and the reference microparticles are present in predetermined amounts or ratios in each reaction container in said kit.

Also provided are kits for use in assays for determining the presence of multiple analytes in a sample, which contain the following elements:

(a) first test microparticles having disposed thereon a first binding molecule which binds the first analyte;

(b) second test microparticles having disposed thereon a second binding molecule which binds the second analyte; and (c) reference microparticles non-reactable with the first and second analytes, the first test and second test microparticles and the first and second binding molecules;

wherein the first and second test microparticles and the reference microparticles are each present in predetermined amounts or ratios in each reaction container in said kit.

In preferred embodiments, the microparticles are provided in dried form, and suitably packaged to facilitate mixing with a sample. For example, the predetermined amounts of each of the dried microparticles may be separately disposed in wells of a multi-well, sealed container, the addition of a fluid sample to which causes the reconstitution of the dried microparticles and the formation of a reaction mixture, which allows a specific binding reaction between the analyte(s) and the respective binding molecule(s) to occur. The dried microparticles may also be provided in admixture in the form of a composition which may be reconstituted upon contact with a sample fluid.

The assay methods of the present invention may be advantageously practiced to determine the presence of the variety of analytes, such as antibodies specific to Rubella, herpes simplex virus (HSV), syphilis, cytomegalovirus, and toxoplasma. A variety of samples may be assayed, including blood and other bodily fluids such as serum, plasma, saliva, cerebrospinal fluid (CSF), urine and eluates of solids.

DETAILED DESCRIPTION OF THE PREFERRED EMBODIMENT

The present invention is directed to assaying a sample to detect the presence of an analyte of interest. By the term "sample", it is meant to include biological fluids such as blood, plasma, serum, saliva, CSF, and urine, and any other type of fluid, cell or material which is suspected of containing an analyte of interest. By "cells", it is meant any sample obtained from a bodily organ or other tissue, e.g. a tumor, from which a cellular suspension can be prepared. By the term "analyte", it is meant any substance for which there exists a specific binding member (i.e., a binding molecule which binds the analyte), or for which a specific binding member can be prepared, and which will bind the specific binding member in an assay. Representative analytes include antigens, haptens, antibodies, and combinations thereof, including proteins, peptides, amino acids, hormones, steroids, vitamins, drugs, nucleic acids and metabolites thereof. Antibodies, antigens, or nucleic acids of interest that may be detected in accordance with the present invention include any antibody, antigen, or nucleic acid which is capable of agglutinating upon contact or reaction with a binding molecule, and particularly antibodies and antigens whose presence in a biological sample is indicative of an inflammatory condition or a disease state. Exemplary antibodies include anti-rubella antibody, anti-HSV I antibody, anti-syphilis antibody, anti-cytomegalovirus antibody, anti-toxoplasma antibody, anti-fungal antibodies, anti-parasite antibodies, and anti-HIV antibodies. Exemplary antigens of interest include proteins, e.g. hormones such as TSH, HCG, $T_4$, glycoproteins, drugs, and microorganisms, e.g., bacteria, viruses, and protozoa, and antigenic fragments thereof, e.g., HBsAg. By the term "hapten", it is meant a low-molecular weight, physiologically active substance, which alone is incapable of producing an antibody response in a mammal, but when bound with a substance which in itself is antigenic, is capable of producing an antibody, as well as reacting with the antibody. Typical haptens include drugs such as androgens, estrogens, progestogens, corticoids, thyroid hormones, physiologically active amines, medicines, and the like, and their metabolic by-products. By the phrase "binding molecule which binds the analyte," it is meant a member of a specific binding pair whereby one of the molecules of the pair, via chemical or physical means, specifically binds to the second molecule, and exhibits negligible cross-reactivity with other substances. Typical binding molecules include antigens, antigen fragments, receptors, nucleic acids, polyclonal or monoclonal antibodies, and fragments or complexes thereof. Such binding molecules specific for a given analyte may be obtained from commercial sources or may be provided in accordance with standard procedures.

To conduct the assays of the present invention, it is first necessary to provide microparticles having disposed thereon a binding molecule which binds the analyte (hereinafter "test microparticles"), and microparticles which are substantially inert to, i.e., non-reactable with, the analyte(s), and the binding molecule(s) (hereinafter "reference microparticles"). The test microparticles, may be prepared from any natural or synthetic material capable of having a binding molecule, e.g., an antigen or antibody, disposed thereon. Such materials include glass, acrylamide or methacrylate, nylon, microscopic oxide powders, latex polymeric materials and their magnetic derivatives, e.g., polymers of olefinically unsaturated monomers such as polystyrene, acrylonitrile and polybutadiene and derivatives and copolymers thereof (see, e.g., Bangs, L. B., *Uniform Latex Particles,* Seragen, Ind., 1984 and U.S. Pat. No. 4,305,925), dextrans, cellulose and derivatives thereof, as well as natural particulate materials such as red blood cells, pollens, liposomes, and bacteria. The reference particles may be prepared from the same materials as the test particles, or from different materials. Also, the reference particles should -be substantially inert to (i.e., non-reactable with) the binding materials disposed on the test particles, as well as the analyte(s). The reference particles may be rendered inert in accordance with known procedures such as chemical treatment. Preferred materials for the reference particles are listed above.

In preferred embodiments, the chemical composition and/or size of the test and reference microparticles are selected so that they are resolvable at the sensitivity level of the detector from each other in the chosen manner in which the non-reacted (i.e., non-agglutinated) test microparticles and the reference microparticles are counted. However, it should be appreciated that any other characteristic or measurable property capable of generating a uniform detector response will provide an appropriate and reliable basis upon which to select microparticles for use in the disclosed assays. Preferably, each of the test microparticles and the reference microparticles is of a uniform size. Where the particles are to be counted by a technique which depends upon particle size to resolve different particles, such as in the case of electronic and various optical counting methods, the test and reference particles should be of different sizes. Also, where several different test particles are used, as in the case of an agglutination assay to simultaneously detect the presence of a plurality of analytes in a given sample, they may be of different sizes. In general, the size of the carrier microparticles is in the range of from about $0.1\mu$ to about $20\mu$, whereas the size of the reference microparticles is in the range of from about $0.1\mu$, to about $20\mu$. These size ranges also depend on the counting technique used and the nature of the binding molecule. Assays which utilize optical counting techniques may also resolve or distinguish between test and reference microparticles based upon their respective refractive indices. It is well known that particles of different compositions will scatter light differently in different directions. See, M. Kerker, *The Scattering of Light and Other Electromagnetic Radiation,* Academic Press, N.Y. 1969, and U.S. Pat. No. 5,369,037 to Hansen et al.

The binding molecules may be disposed on the test microparticles in accordance with standard techniques such as physical (passive) absorption, facilitated (forced) absorption and covalent coupling. For example, the binding molecule may be covalently attached to the test microparticle surface by modification with chemical functional groups capable of protein attachment. U.S. Pat. No. 4,064,080 discloses styrene polymers with terminal aminophenyl groups and proteins attached to them. U.S. Pat. No. 4,181,636 teaches carboxylated latex polymers coupled to immunologically active materials through a water soluble activating agent. U.S. Pat. No. 4,210,723 teaches shell-core latex polymer particles of 0.15–1.5 $\mu$m diameter having free epoxy groups on the particle surfaces. U.S. Pat. No. 4,264,766 is directed to latex polymers having active groups such as carboxyl and amino groups to which water soluble polyhydroxy compounds can be covalently attached, and which upon treatment with an activating agent, e.g., carbodiimide, may be covalently coupled to an immunologically active agent. See also U.S. Pat. Nos. 4,521,521 and 4,305,925. The techniques disclosed in these patents may be used to attach the binding molecules to the test microparticles. In preferred embodiments where the test microparticles are polystyrene particles, the sulfate charge groups which stabilize the particles may be substituted by a variety of other functional groups at the particle surface, such as hydroxyl, carboxyl, amine, acrylamide, and polymeric carboxylate groups, which facilitate the disposition (e.g., coating or adsorption) of the binding molecules on the microparticle surface. See also Seaman G. V. F., ed., *Latex Based Technology in Diagnostics,* Health & Science Communications, Washington, D.C. 20005 (1990). Binding molecule-coated test microparticles may also be obtained commercially.

Figure 1:
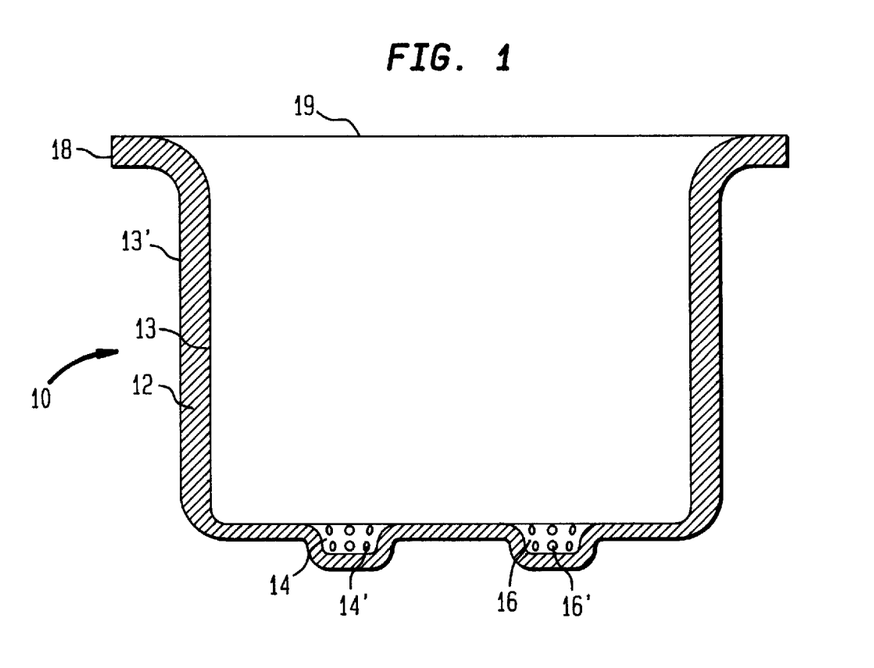
FIG. 1 is cross-sectional view of a multiwell container in which a preferred embodiment of the present invention may be carried out.

The test microparticles and reference microparticles desirably are packaged together, ready for use in a test. A preferred package is a cup as illustrated in FIG. 1. Cup 10 is defined by wall 12 having inner and outer surfaces 13 and 13', respectively. Cup 10 desirably is formed from an inert polymeric material such as polypropylene, polyethylene, or other suitable thermoplastic material. The bottom of inner surface 13 contains recesses or wells 14 and 16, in which dried test microparticles 14' and reference microparticles 16', respectively, are contained. The cup is closed by removable or pierceable sealing element 19, which may be a heat-sealed metal foil or other membrane. The -microparticles can be placed into the wells after drying. More preferably, the microparticles are dispensed into separate wells as slurries and then dried in situ in the wells. The wells maintain the microparticles separate from one another prior to drying. During handling of the container after drying, the microparticles can mix with one another, but such mixing will not evoke a reaction in the absence of a liquid medium. However, this embodiment of the present invention is not limited to the illustrated features. It is not necessary to separate the individual test particles and the referenced microparticles, e.g., to be disposed in separate, individual wells. It is even more preferred that the assay be practiced in a non-recessed or welled container. In addition, the microparticles may be provided in liquid form .

A sample suspected of containing an analyte of interest is then mixed with predetermined amounts of the test microparticles having disposed thereon the binding molecule which binds the analyte, and the reference microparticles under suitable conditions to form a liquid reaction mixture and to allow a measurable reaction between the binding molecule and the analyte to occur. If the sample is itself a liquid, the microparticles may be added to the sample, or vice versa. Alternatively or additionally, the sample and microparticles can be mixed with a liquid diluent, typically an aqueous diluent. In a preferred embodiment, the reaction is conducted in the container illustrated in FIG. 1. To conduct the reaction, seal 19 is pierced or separated from lip 18 of the cup, and he microparticles are reconstituted by the addition of the sample (optionally with aqueous diluent) to be tested, with appropriate diffusion or agitation such as stirring or shaking. Optionally, the reconstituted microparticles are sonicated.

Once a measurable reaction has been allowed to proceed, which, depending upon the nature of the analyte and the amount of sample and microparticles used, will generally range from about 1 minute to about 2 hours, the non-reacted test microparticles and the reference microparticles are counted and compared to each- other to establish a test value. In a preferred embodiment of the present invention, these microparticles are counted cytometrically by passing the suspension through an electronic or optical flow particle analyzer (FPA) which detects particle aggregation by monitoring the size of the individual particles or aggregates thereof as they flow individually through either an electronic or optical sensing zone, respectively. Electronic-type FPA's typically measure the electrical impedance of the reaction mixture by passing the reaction mixture through a narrow orifice and measuring the electrical impedance through the orifice. Where the liquid in the mixture is electrically conductive and the particles are electrically nonconductive, the electrical impedance across the orifice increases when a particle or particle agglomerate passes through the orifice. The degree of increase is directly related to the size of the microparticle or agglutinate, and signals representing particles of different sizes are differentiated from one another.

As discussed below, optical FPAs distinguish particle sizes and the formation of microparticle agglutinates by measuring various characteristics of light scatter of the individual microparticles. Examples of optical FPAs are disclosed in U.S. Pat. Nos. 4,279,617, 4,184,849, 4,191,739, 5,286,452, 5,369,037, and co-pending, commonly owned U.S. patent application Ser. No. 08/473,187. The use of optical FPAs, and particularly those disclosed in U.S. Pat. Nos. 5,286,452 and 5,369,037 and in U.S. patent Application No. 08/473,187, is preferred. In this embodiment, non-reacted test microparticles and reference microparticles may be distinguished on the basis of size and/or refractive index, fluorescence or absorbance.

As noted above, techniques for counting microparticles and microparticle agglutinates of different types are well known, and form no part of the present invention. However, the following description of particle counting and categorizing using an FPA is given for ease of understanding. To conduct an assay of the present invention using an optical FPA, a narrow stream of the reaction mixture is passed through a flow cell illuminated with a beam of light from an incident light source such as a laser. The flow stream configuration and light beam configuration are selected so that individual microparticles or individual microparticle agglutinates pass through the light beam one after the other, and so that only one microparticle or agglutinate is in the beam at any time. Light which is scattered, reflected or emitted by each microparticle or agglutinate as it passes through the beam of incident light is detected by appropriate sensors to yield a signal for each microparticle or agglutinate. The characteristics of individual signals are different for the different types of microparticles and agglutinates. The various types of microparticles or agglutinates are counted by categorizing each signal as representative of a particular type of microparticle or agglutinate. For example, in a light-scattering FPA, the scattered light intensity produced by each microparticle or agglutinate is directly related to the size of the particle or agglomerate, and to the refractive index of the microparticle or agglutinate. Therefore, scattered light signals within one range of intensities represent single non-agglutinated test microparticles, whereas signals in another range represent the non-agglutinated reference microparticles. By counting the signals within each range, the number of non-agglutinated test microparticles and non-agglutinated reference microparticles in the reaction mixture may be counted. Signals in yet another range of intensities represent agglutinates of two test microparticles (i.e., dimers), and signals in still other ranges represent agglutinates of three or more test microparticles (i.e., trimers and multimers). Signals in a further range of intensities represent agglutinates of two reference microparticles (i.e., dimers), and signals in an even further range represent agglutinates of three reference microparticles (i.e., trimers, etc.), collectively referred to as self-agglutinates. In this manner, the number of test microparticles and reference microparticles may be determined by also counting those microparticles that are in the form of self-agglutinates such as dimers and trimers.

The signal classification and counting procedure may be performed by determining a statistical distribution such as a histogram based on a particular characteristic (e.g., pulse height) of the light scatter generated from each type of microparticle. The histogram serves as a statistical summary of the numbers and types of microparticles detected by the FPA, by creating a frequency distribution of microparticles. In a preferred embodiment of the present invention, a histogram is created by digitizing the peak height of the pulses generated from each illuminated microparticle, using an analog-to-digital converter, and transferring each such digitized value (e.g., expressed in volts) that lies above an arbitrarily established value (e.g., to eliminate false triggering due to noise) to a computer program. This step may be accomplished using a suitable collection scheme such as direct memory access involving at least one data collection cycle. The program plots the number of signals as a function of digitized value such as voltage. A window or range which encompasses the expected spread in pulse height values, is defined for each type of microparticle or agglutinate. The collection scheme may be modified to establish a predetermined number of counts for any single window. In a more preferred embodiment, once the histogram is collected, different microparticle populations are identified by establishing pre-defined windows or by automatic peak seeking and classification. The foregoing description of FPA operation, and of particle classification and counting techniques, is merely exemplary. Other FPA techniques rely on signals other than scattered light, such as light emitted by fluorescent particles or light reflected by the microparticles. Still others use combinations of characteristics to differentiate signals, such as the relationship between fluorescent light emitted by each particle and the light scattered by such particle. Any of the known techniques for counting and categorizing microparticles can be utilized.

The sum of the counts (i.e., individual data points) in the windows defining the non-reacted test microparticles and the reference microparticles is then calculated. To the extent that non-specific agglutination of reference microparticles occurs, the accuracy of the assays may be further enhanced by counting any such agglutinates and multiplying by the number of individual reference microparticles in each type of agglutinate.

The number of non-reacted test microparticles is then compared to the number of reference microparticles to establish a test value. In a preferred embodiment of the present invention, the test value is a ratio of the number of non-reacted test microparticles to the number of reference microparticles. However, other test values based on these numbers may be used such as the difference between the number of unagglutinated test microparticles and the number of reference microparticles. In a preferred embodiment, the test value is compared to a control value for a non-reactive sample (which does not contain the analyte), which is determined in accordance with the same procedure described above, and a change value is calculated from the test value and the control value. In a preferred embodiment, the change value is calculated as a decrease in test microparticles (relative to the original, predetermined population), expressed as a percentage. In accordance with this preferred embodiment wherein the test and control values are ratios, a change ratio is calculated by subtracting the test ratio from the control ratio, dividing the difference by the control ratio, and multiplying by 100. In a more preferred embodiment of the present invention, the change ratio is calculated by dividing the control ratio by the test ratio, such that the change ratio increases with samples containing greater amounts of analyte. The change value may be compared to threshold limits generated in accordance with standard procedures, e.g., testing known positive and negative samples. For example, an assay is considered positive and the presence of the analyte in the fluid sample is confirmed if the change value is above an upper threshold limit. Conversely, a change value that is below the lower threshold limit is indicative of a negative result.

The assays of the present invention may also be used to detect a plurality of analytes in a given sample. To conduct an assay in accordance with this embodiment, it is necessary to provide test microparticles specific for each analyte to be determined, and which are resolvable as to each other and the reference microparticles in the given counting method. For example, in the case of an assay for determining the presence of two analytes in a sample, it would be necessary to provide first test microparticles having disposed thereon a first binding molecule which binds the first analyte, and second test microparticles having disposed thereon a second binding molecule which binds the second analyte, as well as the reference microparticles. Test values for each of the different non-reacted test microparticles are calculated based on the same number of reference microparticles.

As in the case of a single analyte determination, the reactants for a multi-analyte assay may be processed to a dry powder or tablet, individually, or together in admixture to form a composition. Alternatively or additionally, the reactants may be packaged in a kit which may include a container suitable for reconstituting the microparticles upon mixing with the sample and optional substances such as liquid diluents, and the like, and conducting the binding molecule-analyte reaction.

In the preferred embodiments of the present invention described above, which involves the optical cytometric analysis of samples, the peak height of scattered light produced by a microparticle or agglutinate is used as the criterion for classifying the microparticle or agglutinate as belonging to a particular type, such as an unreacted test microparticle, reference microparticle, agglutinate of test microparticles or the like. Other light scatter properties may also be used, including pulse amplitude, pulse width, the product of pulse amplitude and pulse width, integrated pulse area, or some linear or non-linear function of these parameters at the same or different scattering angles. Light scatter signals generated by each type of particle passing through the FPA may be measured at low angles in the forward direction (i.e., from about 3 to about 7 degrees from the axis of the incident beam of light), from about 85 to about 95 degrees (i.e., substantially side-scatter signals), or from about 95 to about 180 degrees (i.e., back scatter signals).

Even more generally, however, the assays out of present invention may be carried out wherein the non-reacted test microparticles and the reference microparticles are counted by measuring an electronic property of the reaction mixture such as resistive-pulse (impedance), capacitance or resistance. The resistive-pulse technique consists of suspending the particles in an electrolytic solvent so that each particle which enters the pore displaces a portion of solvent resulting in a change in the pore's electrical conductivity. Since the change in conductivity is proportional to the volume of the particle, the size distribution of the sample is accumulated by sending thousands of particles through the pore. Because the measurement and subsequent signal processing is rapid, statistically meaningful distributions can be obtained in a short time, often in minutes. See, e.g., U.S. Pat. No. 4,191,739. An example of a capacitance-based assay system is disclosed in U.S. Pat. No. 4,072,576. Other assay systems based upon electrical measurements of particles are disclosed in U.S. Pat. No. 5,284,748. The methods of the present invention may also be practiced using non-cytometric techniques, such as image analysis.

As noted above, it is not necessary to count agglutinates of test microparticles; information concerning the extent of agglutination is obtained from the count of non-agglutinated test microparticles remaining after reaction, taken in comparison with the number of reference microparticles. However, if the agglutinates are counted, the count can be used as a cross-check on the assay. Thus, if the ratio of non-agglutinated test microparticles to reference microparticles in the reacted mixture is substantially lower than the corresponding ratio in an unreacted control mixture, indicating substantial agglutination of the test microparticles, the count of agglutinated microparticles should be high. If it is not, the computer can issue an error signal.

The invention will be further described by reference to the following detailed examples. These examples are provided for purposes of illustration only, and are not intended to be limiting unless otherwise specified.

EXAMPLES

Example 1

Assay for the simultaneous detection of antibodies specific to Toxoplasma gondii, Rubella virus and Cytomegalovirus (CMV)

Preparation of Assay Reagents

Polystyrene latex particles having diameters of 1.1, 1.6$\mu$, 1.7$\mu$ and 1.9$\mu$, were obtained from Interfacial Dynamics, Inc., (Portland, Oreg.). Toxoplasma gondii, Rubella virus, and CMV antigen preparations were obtained from Ross Southern Laboratories (Salt Lake City, Utah), Viral Antigens, Inc. (Memphis, Tenn.) and Advanced Biotechnologies (Columbia, Md.), respectively. The three types of antigen were disrupted with detergent and sonication and diluted with carbonate/bicarbonate solution at pH 9.6 as follows: Toxoplasma antigen at 50 $\mu$g per mL, rubella at 10 $\mu$g per mL, and CMV at 50 $\mu$g per mL. Washed polystyrene particles were suspended at a 2% W/V concentration in the same buffer and equal parts of particles and antigens were mixed: 1.6$\mu$ particles and Toxoplasma solution, 1.7$\mu$ particles and rubella solution and 1.9$\mu$ particles and CMV solution. The mixtures were rocked at room temperature: 2 hours for Toxoplasma and rubella and 1 hour for CMV. Excess antigen was removed by centrifugation and the three coated particle suspensions each washed three times in 0.1M glycine pH 7.0, 1% BSA, 5% sucrose and 0.1% sodium azide. The washed particles were then resuspended in the same buffer at 1% W/V.

To prepare the internal reference particles (IRP), the 1.1$\mu$ polystyrene particles were washed and resuspended in 0.1% SDS and then rocked for 1.5 hours. The particles were then washed three times in carbonate/bicarbonate and then three times in 0.1M glycine pH 7.0, 1% BSA, 5% sucrose and 0.1% sodium azide, and then resuspended in the same buffer at 1% W/V.

A mixture of the four types of coated particles was then dried in individual cups. Each of the coated particle types was first sonicated briefly to disperse any aggregates and then a mixture of the four particle types was made. For each cup to be filled, the following aliquots of the 1% W/V coated particle suspensions are mixed: IRP: 3.5 $\mu$L; Toxoplasma: 15 $\mu$L; Rubella: 10 $\mu$L; CMV 20 $\mu$L. This mixture was centrifuged to concentrate the mixture to 20 $\mu$L per cup to be filled. The mixture was then sonicated briefly to disperse any aggregates. Twenty $\mu$l of the mix were then added to each of 1500 cups.

The cups containing the particle mixtures were then dried overnight in a 37° C. vacuum oven. A metal stir bar was then added to each cup before the cup was sealed. The sealed cups were stored at room temperature until used.

To conduct the assay, the required number of cups was placed in the Copalis™ One Immunoassay instrument (maximum number of cups is 24 per run). The instrument pierced the cup seal, added 180 $\mu$L of reaction buffer (0.5M potassium bromide, 0.1M glycine, pH 9.0, 1% BSA, 0.2% sodium azide, 1.5% polyethylene glycol, MW 6000–8000). The instrument briefly sonicated each cup to disperse any aggregates and then added a sample to be tested to each cup, 20 $\mu$L of either human serum or control material. Controls consisted of samples with known presence or absence of antibodies specific for Toxoplasma gondii, rubella and CMV. A sample with no reactivity (1% $\beta$-lactoglobulin) was used to obtain the particle counts for the negative reaction control discussed in the section below on analysis. As sample was added to each cup, the instrument initiated notion of the stir bar in that cup, beginning a ten minute incubation period.

Analysis of Results

After the contents of each cup had been agitated for ten minutes, the instrument removed an aliquot from each cup and counted the number of non-reacted particles (i.e., monomers) remaining for each of the Toxoplasma (designated "A" in Table 1), rubella ("B") and CMV ("C") relative to the internal reference particles. The counting of the nonreacted test particles in each cup was terminated when 10,000 internal reference particles had been counted. These numbers were then used to perform the calculations set forth in Table 1.

TABLE 1

$$\frac{A/10,000_{Negative\ Reaction\ Control}}{A/10,000_{test\ sample}} \times 100 = \text{Result for toxoplasma } gondii \text{ antibody presence}$$

$$\frac{B/10,000_{Negative\ Reaction\ Control}}{B/10,000_{test\ sample}} \times 100 = \text{Result for rubella antibody presence}$$

$$\frac{C/10,000_{Negative\ Reaction\ Control}}{C/10,000_{test\ sample}} \times 100 = \text{Result for CMV antibody presence}$$

The same procedure was conducted using several known antibody negative and antibody positive samples in order to establish cutoff or threshold values for each of the three antibody tests. The cutoff values for toxoplasma gondii, Rubella, and CMV are set forth in Table 2.

TABLE 2

| ASSAY COMPONENT | CUTOFF VALUE (CTR) | INTERPRETATION |
| --- | --- | --- |
| Toxoplasma gondii Antibody | <111 | Negative |
|  | ≧111 | Positive |
| Rubella Antibody | <114 | Negative |
|  | ≧114 | Positive |
| CMV Antibody | <111 | Negative |
|  | ≧111 | Positive |

The results for the unknown samples, interpreted in view of the cutoff values, are set forth in Table 3.

TABLE 3

| Sample Type[1] | Toxoplasma gondii Result | Inter. | Rubella Result | Inter. | CMV Result | Inter. |
|---|---|---|---|---|---|---|
| T−,R−,C− | 100 | − | 98 | − | 100 | − |
| T+,R−,C− | 140 | + | 100 | − | 99 | − |
| T−,R+,C− | 106 | − | 153 | + | 103 | − |
| T−,R−,C+ | 99 | − | 107 | − | 286 | + |
| T+,R+,C− | 150 | + | 144 | + | 99 | − |
| T−,R+,C+ | 105 | − | 356 | + | 175 | + |
| T+,R−,C+ | 154 | + | 106 | − | 194 | + |
| T+,R+,C+ | 166 | + | 280+ | + | 197 | + |

Legend
[1]The actual antibody status of these samples was determined by testing them on commercialized tests for detecting the antibodies for Toxoplasma gondii, rubella and CMV.

All publications and patent applications mentioned in this specification are indicative of the level of skill of those skilled in the art to which this invention pertains. All of these publications and patent applications are herein incorporated by reference to the same extent as if each individual publication and patent application were specifically and individually indicated to be incorporated by reference.

Various modifications of the invention described herein will become apparent to those skilled in the art. Such modifications are intended to fall into the scope of the appended claims.

We claim:

1. An assay for determining the presence of an analyte in a sample, comprising the steps of:
   (a) mixing the sample and predetermined amounts of test microparticles having disposed thereon a binding molecule which binds the analyte, and reference microparticles non-reactable with the analyte and the binding molecule, to form a reaction mixture and allow for the binding molecule to bind the analyte;
   (b) counting the numbers of the non-reacted test microparticles and the reference microparticles optically or electronically; and
   (c) comparing the number of non-reacted test microparticles to the reference microparticles to thereby establish a test value so that the presence of the analyte in the sample may be determined.

2. The assay of claim 1, further comprising the step (d) of comparing said test value to a control value for a non-reactive sample.

3. The assay of claim 2, wherein said step (d) of comparing comprises the step (e) of calculating a change value from said test value and said control value.

4. The assay of claim 3, wherein said step (e) comprises the step (f) of obtaining the difference between said control value and said test value.

5. The assay of claim 4, wherein said step (f) further comprises the step (g) of dividing said difference by said control value.

6. The assay of claim 3, wherein step (e) comprises the step (h) of dividing said control value by said test value.

7. The assay of claim 1, wherein said step (c) comprises the step (i) of calculating a ratio between the number of non-reacted test microparticles and the number of reference microparticles.

8. The assay of claim 1, wherein said step (b) of counting comprises measuring the impedance of said reaction mixture.

9. The assay of claim 8, wherein said step (b) of counting further comprises measuring the resistance of said reaction mixture.

10. The assay of claim 1, wherein said step (b) of counting comprises measuring the capacitance of said reaction mixture.

11. The assay of claim 1, wherein said step (b) of counting comprises measuring cytometrically a light scatter characteristic of the non-reacted test microparticles and the reference microparticles.

12. The assay of claim 1, wherein said step (b) of counting comprises counting the number of said reference microparticles that are in the form of self-agglutinates.

13. The assay of claim 1, wherein the test microparticles, the reference microparticles, or both the test microparticles and the reference microparticles comprise a polymeric material.

14. The assay of claim 13, wherein said polymeric material comprises polystyrene or a derivative thereof.

15. The assay of claim 14, wherein the latex polymer comprises polybutadiene or a derivative thereof.

16. The assay of claim 13, wherein the test microparticles comprise a polymeric material having surface functional chemical groups.

17. The assay of claim 16, wherein the surface functional chemical groups comprise acrylamide groups.

18. The assay of claim 1, wherein said analyte is an antibody.

19. The assay of claim 18, wherein the binding molecule is an antigen which binds the analyte antibody.

20. The assay of claim 19, wherein the analyte antibody is anti-Rubella antibody.

21. The assay of claim 20, wherein the binding molecule comprises inactivated antigenic fragments of Rubella virus.

22. The assay of claim 18, wherein the analyte antibody is anti-HSV I antibody.

23. The assay of claim 22, wherein the binding molecule comprises inactivated antigenic fragments of HSV I.

24. The assay of claim 18, wherein the analyte antibody is anti-syphilis antibody.

25. The assay of claim 18, wherein the analyte antibody is anti-cytomegalovirus antibody.

26. The assay of claim 25, wherein the binding molecule comprises inactivated antigenic fragments of cytomegalovirus.

27. The assay of claim 18, wherein the analyte antibody is anti-toxoplasma antibody.

28. The assay of claim 1, wherein the sample comprises blood.

29. The assay of claim 1, wherein the sample comprises serum.

30. The assay of claim 1, wherein the sample comprises plasma.

31. The assay of claim 1, wherein the sample comprises saliva.

32. The assay of claim 1, wherein the sample comprises cerebrospinal fluid.

33. The assay of claim 1, wherein the sample comprises urine.

34. The assay of claim 1, wherein the sample comprises cells obtained from a bodily organ or tissue.

35. An assay for determining the presence of at least two analytes in a sample, comprising the steps of:
   (a) mixing the sample and predetermined amounts of first test microparticles having disposed thereon a binding molecule which bind a first analyte, second test microparticles having disposed thereon a binding molecule which binds a second analyte, and reference microparticles non-reactable with the first and second analytes and the first and second binding molecules, to form a reaction mixture and allow for the first binding molecule to bind the first analyte and the second binding molecule to bind to the second analyte;

(b) counting the numbers of the non-reacted first test microparticles, the non-reacted second test microparticles, and the reference microparticles optically or electronically; and (c) comparing the number of non-reacted first test microparticles to the reference microparticles to thereby establish a first test value, and comparing the number of non-reacted second test microparticles to the reference microparticles to thereby establish a second test value, so that the presence of the first and second analytes in the sample may be determined.

36. An assay for determining the presence of an analyte in a sample, comprising the steps of:

(a) mixing the sample and predetermined amounts of test microparticles having disposed thereon a binding molecule which binds the analyte, and reference microparticles non-reactable with the analyte and the binding molecule, to form a reaction mixture and allow for the binding molecule to bind the analyte;

(b) counting the numbers of the non-reacted test microparticles and the reference microparticles; and (c) comparing the number of non-reacted test microparticles to the reference microparticles to thereby establish a test value so that the presence of the analyte in the sample may be determined.

37. An assay for determining the presence of at least two analytes in a sample, comprising the steps of:

(a) mixing the sample and predetermined amounts of first test microparticles having disposed thereon a binding molecule which bind a first analyte, second test microparticles having disposed thereon a binding molecule which binds a second analyte, and reference microparticles non-reactable with the first and second analytes and the first and second binding molecules, to form a reaction mixture and allow for the first binding molecule to bind the first analyte and the second binding molecule to bind to the second analyte;

(b) counting the numbers of the non-reacted first test microparticles, the non-reacted second test microparticles, and the reference microparticles; and (c) comparing the number of non-reacted first test microparticles to the reference microparticles to thereby establish a first test value, and comparing the number of non-reacted second test microparticles to the reference microparticles to thereby establish a second test value, so that the presence of the first and second analytes in the sample may be determined.

* * * * *

UNITED STATES PATENT AND TRADEMARK OFFICE
CERTIFICATE OF CORRECTION

PATENT NO. : 5,858,648
DATED : January 12, 1999
INVENTOR(S) : Steel et al.

It is certified that error appears in the above-identified patent and that said Letters Patent is hereby corrected as shown below:

```
Column 2, line 10, after "of" insert --an--.

Column 2, line 59, delete "-".

Column 6, line 2, delete "-".

Column 7, line 19, delete "-".

Column 7, line 56, delete "-".

Column 9, line 16, "values, is" should read --value is--.

Column 10, line 47, after "of" insert --the--.

Column 11, line 28, "1.1," should read --1.1µ,--

Column 12, line 21, "notion" should read --motion--.

Column 14, line 63, "bind" should read --binds--.

Column 16, line 8, "bind" should read --binds--.
```

Signed and Sealed this

Seventh Day of September, 1999

Attest:

Q. TODD DICKINSON

*Attesting Officer*     *Acting Commissioner of Patents and Trademarks*